United States Patent [19]

Gobran

[11] Patent Number: 5,629,063
[45] Date of Patent: May 13, 1997

[54] REPOSITIONABLE TAPE CLOSURE SYSTEM FOR A THIN FILM ARTICLE

[75] Inventor: Ramsis Gobran, Roseville, Minn.

[73] Assignee: Minnesota Mining and Manufacturing Company, St. Paul, Minn.

[21] Appl. No.: 449,031

[22] Filed: May 24, 1995

Related U.S. Application Data

[62] Division of Ser. No. 333,499, Nov. 2, 1994.

[51] Int. Cl.$^6$ .................................................. A61F 13/60
[52] U.S. Cl. .................. 428/40.1; 428/41.9; 428/42.1; 428/195; 428/201; 428/202; 428/205; 428/220; 428/352; 428/354; 428/356; 428/906; 604/385.1; 604/389; 604/390
[58] Field of Search ........................... 428/40, 906, 195, 428/201, 202, 205, 220, 352, 354, 356, 40.1, 41.9, 42.1; 604/385.1, 389, 390

[56] References Cited

U.S. PATENT DOCUMENTS

| | | | |
|---|---|---|---|
| 2,532,011 | 11/1950 | Dahlquist | 428/40 |
| 3,853,595 | 12/1974 | Pedginski | 428/40 |
| 4,022,211 | 5/1977 | Timmons | 604/361 |
| 4,895,746 | 1/1990 | Mertens | 428/40 |
| 5,429,631 | 7/1995 | Grenier | 604/385.1 |

FOREIGN PATENT DOCUMENTS

| | | |
|---|---|---|
| 232025 | 10/1994 | Taiwan . |
| WO92/01759 | 2/1992 | WIPO . |
| WO92/08763 | 5/1992 | WIPO . |
| WO93/06182 | 4/1993 | WIPO . |
| WO93/11728 | 6/1993 | WIPO . |

*Primary Examiner*—Nasser Ahmad
*Attorney, Agent, or Firm*—Gary L. Griswold; Walter N. Kirn; William J. Bond

[57] ABSTRACT

A pressure-sensitive adhesive closure system for a disposable diaper, or the like, in which a pressure-sensitive adhesive fastening tab releasably attaches to a non-blocking thin diaper backsheet which has been treated to raise the surface energy and pattern printed, preferably in a polar solvent, in a discrete area with a release material. The release material prevents the backsheet from blocking in roll form and allows the pressure-sensitive adhesive fastening tab to be removed from the backsheet without destruction of the backsheet.

9 Claims, 2 Drawing Sheets

5,629,063

REPOSITIONABLE TAPE CLOSURE SYSTEM FOR A THIN FILM ARTICLE

This is a division of application Ser. No. 08/333,499 filed Nov. 2, 1994, pending.

BACKGROUND AND FIELD OF THE INVENTION

The present invention relates to improved disposable articles such as diapers, incontinent products, disposable garments, feminine hygiene products, and the like, having a refastenable pressure-sensitive adhesive fastening tape tab system.

Disposable diapers or incontinence articles, and other disposable garments requiring liquid holdout, are typically made with a liquid impermeable layer. This liquid impermeable layer is generally the outermost layer in the disposable garment. In order to facilitate the wearability and conformability of the disposable garment and minimize costs the liquid impermeable layer typically is an extremely thin film, or laminate with a thin film layer, generally formed of a thermoplastic polymer such as a polyolefin like a polyethylene polymer, copolymer or blend. This same thin polymer film is also generally used as the adhesion surface to which a pressure-sensitive adhesive fastening tab is adhered in order to effect closure of the disposable diaper or other garment. Typically one end of the pressure-sensitive adhesive fastening tab is permanently adhered to one edge region of the garment on the polymer film with the second opposing end of the fastening tab preferably designed to removably attach to an outer surface of the garment adjacent to an opposing edge of the garment. This second or free end of the fastening tab would typically adhere to the thin thermoplastic film or film layer forming the liquid impermeable layer.

A problem with the above system is that in order to provide a secure permanent attachment at the fastening tab first end, the fastening tab pressure sensitive adhesive is sufficiently aggressive such that if the second free end of the fastening tab is removed from the disposable garment it causes the thin polymer film or film layer to tear. Various solutions have been proposed in the art to address this problem. For example, it has been proposed to increase the tensile strength of the diaper backsheet such as by increasing the thickness of the backsheet, using polymers that have higher tensile strengths, or some combination thereof; U.S. Pat. No. 5,147,346 (coextruded backsheet having a high modulus strengthening layer), European Patent No. 256 885 B1 (proposes a diaper backsheet comprising a resin blend of polypropylene and low density polyethylene having a thickness of from 1 to 1.5 mils., a thickness range greater than that for typical commercial backsheets, and a tensile strength of at least 550 grams), U.S. Pat. No. 5,084,039 (proposes a blend of polyethylene and an anti pop-off material, such as an ethylene propylene copolymer) and U.S. Pat. No. 4,880,422 (proposes a diaper backsheet formed from a blend of polypropylene and polyethylene to increase tape tab fastening adhesion and increase tensile strength). Although these stronger backsheets are less resistant to tearing, they are also stiffer and less conformable and significantly more costly than a typical thin diaper backsheet material.

It has also been proposed to decrease the fastening tape tab adhesive peel strength, by use of a less aggressive or less tacky pressure-sensitive adhesive. Although this may decrease the occurrence of tearing of the diaper backsheet, it also significantly increased the possibility that the tape tab could pop-off or fail during use. Generally, it was found difficult to match a pressure-sensitive adhesive to available thin diaper backsheets to provide the desired levels of adhesion performance under a variety of conditions, refastenability without tearing and backsheet conformability and cost.

As an alternative to strengthening the entire diaper backsheet there have been numerous proposals to strengthen just the portion of the backsheet which is adhered to the fastening tape tab. For example, U.S. Pat. No. 3,867,940 (Mesek) proposes reinforcing the diaper backsheet with a scrim or film attached to the inner or outer face of the diaper backsheet at those locations where the diaper fastening tape tab is adhered. This reinforcement is to prevent the backsheet from being torn or distorted while the diaper is being worn or adjusted by the parent (e.g., by removing and adjusting the location of the tape tab). A variation on this is proposed by Japanese Utility Model No. 74910 (1982), which proposes using a small pressure-sensitive adhesive tape attached only at the specific edge location of the diaper where the diaper fastening tape tab free end is most likely to be releasably attached.

Larger areas of reinforcement (as in Mesek), at only the location where the fastening tape tab free end is attached (as in the above Japanese Utility Model No. 74910) are proposed, for example, in U.S. Pat. No. 4,643,730, which proposes a radiation curable coating on an inner face of the diaper backsheet. Similarly, U.S. Pat. No. 4,296,710 proposes coating an inside surface of the diaper backsheet with a hot-melt adhesive to provide a large area of reinforcement. U.S. Pat. No. 4,210,144 likewise proposes reinforcing the inner face of the diaper backsheet with a coating, such as a hot-melt adhesive. European Patent No. 80647 B1 proposes gluing a thin plastic material on an outside face of the diaper backsheet, which is also taught in UK Patent No. 2,129,689 B, which proposes gluing one or more plastic strips to the outside front portion of the diaper, which plastic strips are preferably embossed to control the level of adhesion by the diaper fastening tape tab.

Japanese Patent Kokai No. 64-77604 and Utility Model No. Showa No. 64-37405 proposes coating the outside surface of a diaper backsheet with a heat-curable silicone release material and long chain alkyl release material, respectively, to enable the diaper fastening tape tabs to be adhered and reattached.

The invention addresses providing an improved system for releasably and repeatedly attaching a high tack conventional diaper fastening tape to thin films and the like such as used as a diaper backsheet.

DETAILED DESCRIPTION OF THE INVENTION

The invention low-adhesion printed backsheet adhesive closure system will be described with reference to a conventional baby diaper, however, such a closure system could be used in other disposable applications using adhesive fastening tabs, such as adult incontinent garments, disposable medical gowns, caps, packaging systems, feminine hygiene articles, and the like.

Figure 1:
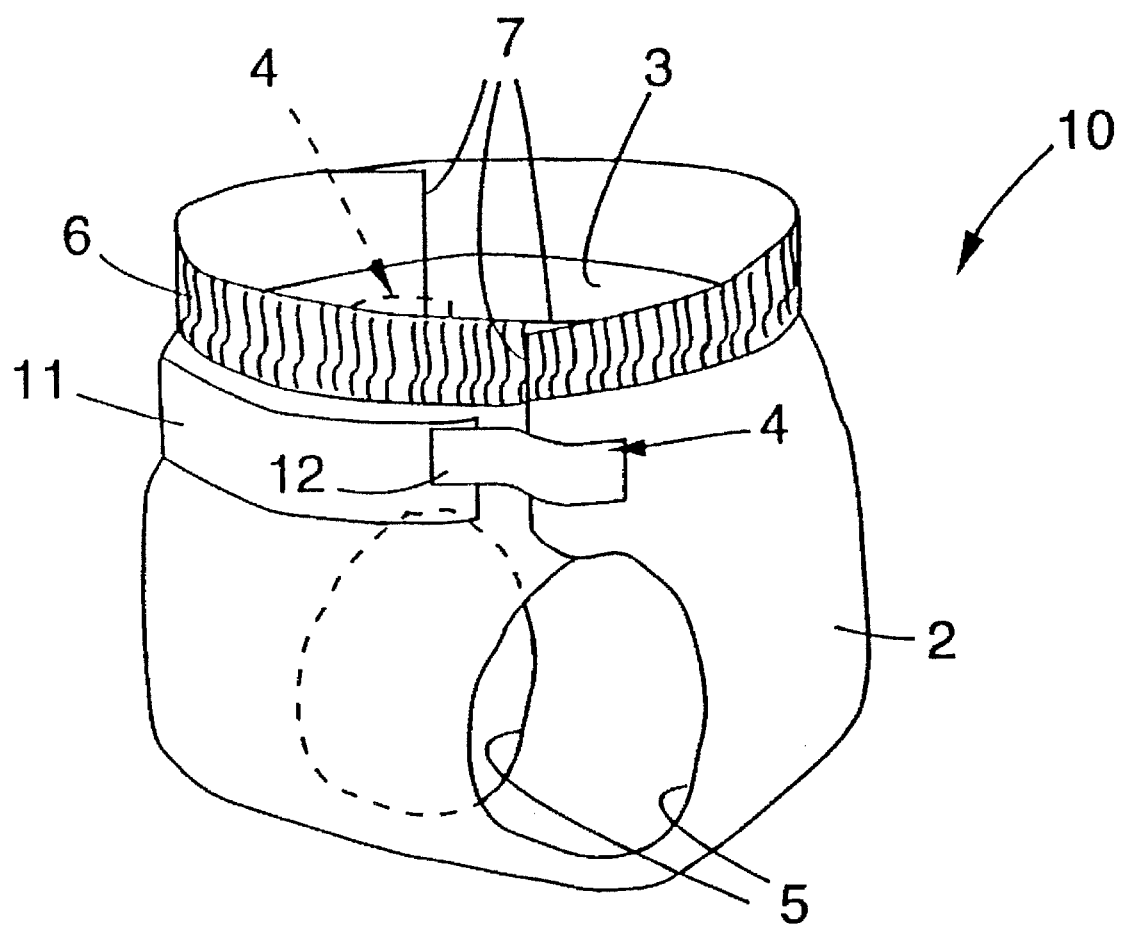
FIG. 1 is a perspective view of a conventional diaper construction using the invention low-adhesion coating, as it would look when placed on a wearer.

A conventional diaper construction is depicted in FIG. 1. The diaper 10 is provided with a thin liquid-impermeable outer backsheet 2 and a liquid-permeable inner coversheet 3. Between the backsheet 2 and inner coversheet 3 is an absorbent core (not shown). Adhesive fastening tape tabs 4 are provided at two laterally opposed side edge regions 7 of the backsheet 2 at a first end of the diaper. At a second end of the diaper on the backsheet 2 is provided a low-adhesion printed coating 11 permanently bonded to the outside face of the thin diaper backsheet 2 providing a surface to which the free ends 12 of the fastening tape tabs 4 can be adhered, removed and repeatedly reattached in the same location. The low-adhesion coating is located adjacent an edge region 7 of the second diaper end so that when the free end 12 of a fastening tape tab 4 is adhered to the low-adhesion coating, two edge regions 7 at opposing ends of the diaper will overlap to effect closure of the diaper. When the free end 12 of a fastening tape tab 4 is attached to the low-adhesion printed coating 11, there is formed a leg opening 5, which is typically provided with elastic means to form a sealing engagement with the wearer's legs. The diaper may also be elasticized around the waist portion to further provide sealing engagement with the wearer by elasticized portions 6. Prior to use, the adhesive surface on the free end 12 of a adhesive fastening tape tab 4 is protected from contamination by a release-coated paper or a release-coated tape, which can be provided adjacent the corner of an edge region 7 and the first end and on the inner coversheet 3.

Figure 2:
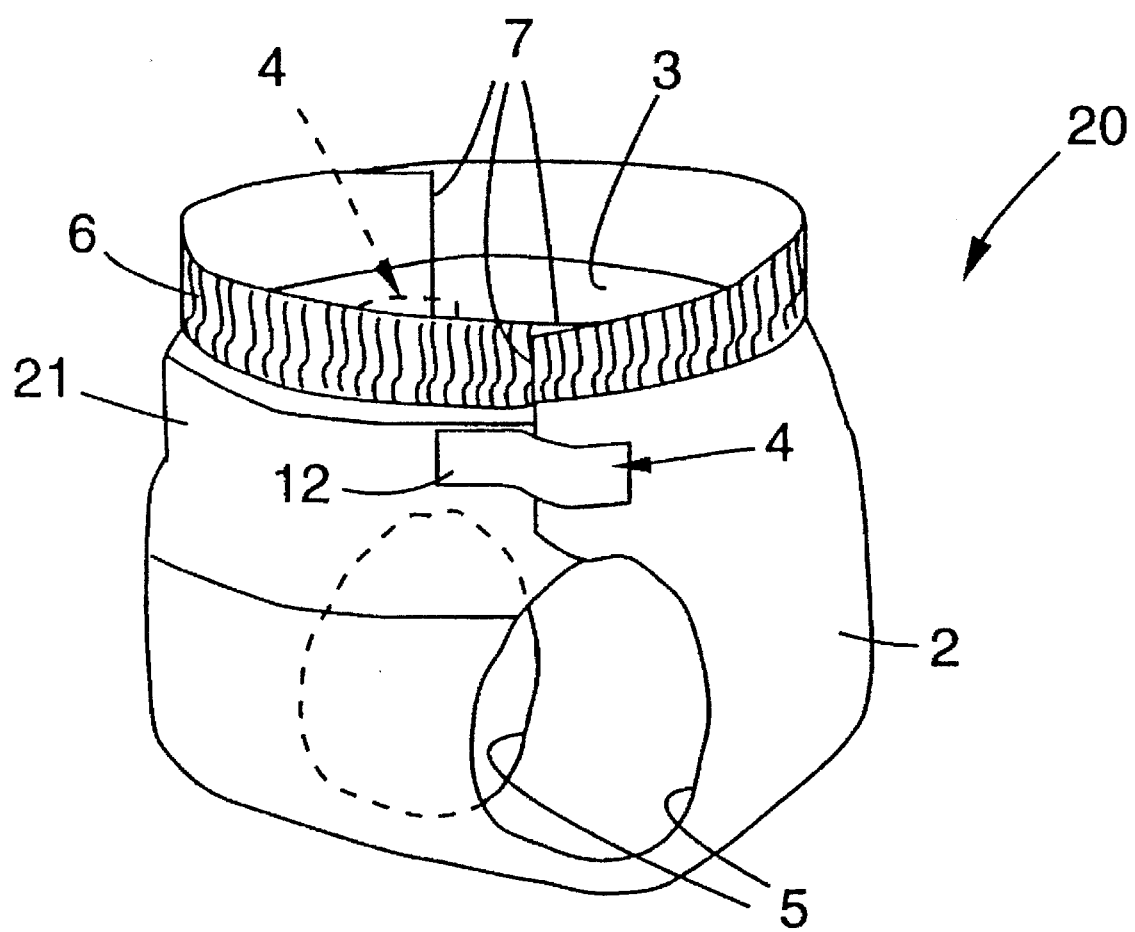
FIG. 2 is a perspective view of a conventional diaper construction using another embodiment of the invention.

The low-adhesion printed coating 11 can be in the shape of a single strip, or region, or multiple strips, or regions(e.g., one for each fastening tab free end 12). A strip is a discrete area of the backsheet printed with the low-adhesion material. The strip(s) 11 should be located so that a fastening tape tab free end 12 would adhere to the strip when the diaper is fitted on the wearer. A strip can be any suitable size. A larger single strip 21 and diaper 20 is shown in FIG. 2. Larger strips present larger target areas for the user to place the free end of the fastening tab with less risk of adhering to a portion of the backsheet without the low-adhesion or release printed coating.

The backsheet web 2 is of conventional design and would typically be a water impermeable thermoplastic film such as a polyolefin film, such as a polyethylene polymer film or a blend of a polyethylene and another polyolefin or thermoplastic polymer, or a coextruded film, as are known in the art. The backsheet could also be in the form of a laminate of two or more films or a film and a nonwoven or woven material or the like. Generally, a backsheet 2 film is thin, e.g., a film of less than 50 microns thick, preferably less than 35 microns thick.

The outer face of the backsheet 2 is treated to have a surface energy of greater than about 33 dynes/cm, preferably greater than about 40 d/cm. This surface energy can be obtained by suitable selection of polymers, additives or the like for the material forming the outer surface of the backsheet or by post-web formation techniques such as corona treatment, flame treatment, chemical primers or the like. Preferred is corona treatment.

The low-adhesion printed coating is generally an aqueous or polar solvent based low-adhesion material such as can be applied with conventional printing techniques such as offset printing, gravure printing, flexographic printing, rotary screen printing, ink jet printing or the like. Preferred is flexographic and gravure printing. Other printable release materials are also possible such as curable 100 percent solid systems. The printed low-adhesion material is preferably applied as a continuous pattern (i.e., a discrete area 100 percent covered with the low-adhesion material) but intermittent or discontinuous printed patterns over the discrete area printed are also possible. If desired, the backsheet film can be ink printed, prior to the low-adhesion printing, with an aesthetic design or figure(s), in random or repeating patterns over all or a portion of the backsheet. The ink printing can be of any conventional aqueous or polar solvent based ink, such as those disclosed in U.S. Patent Nos.: 5,302,193; 5,310,887; and 5,296,275.

The low-adhesion material is any that can be suitably printed from a polar or aqueous solvent such that the solvent will not distort or dissolve the thermoplastic backsheet. Suitable low-adhesion materials can be printed out of solutions, dispersions, emulsions or suspensions.

The pressure-sensitive adhesive selected for the fastening tape tab is suitably one that will provide a tape tab that will adhere to the backsheet more strongly than to the printed low-adhesion material, generally providing a peel adhesion at least 1.2 times higher to the backsheet than to the low-adhesion printed area. The adhesion of the tape tab to the low-adhesion printed area can be any functional level of adhesion for the particular contemplated end use. For diapers, the fastening tape tab 135° peel (described below) is generally at least 70 grams/25.4 mm (inch) and is preferably at least 100 grams/25.4 mm. Repeated application of the fastening tape tab to the same location or different locations on the low-adhesion printed area provides 135° peel values within 30 percent of the initial peel value preferably within 20 percent of the initial peel value, at room temperature.

The adhesives can be any conventional pressure-sensitive adhesive composition, however, preferably is a rubber-resin based adhesive.

The pressure-sensitive adhesive on the fastening tab is preferably a tackified elastomer where the elastomer is an A-B type block copolymer, wherein the A blocks and the B blocks are configured in linear, radial, or star configurations. The A block is a mono alkenyl arene, preferably polystyrene, having a molecular weight between 4,000 and 50,000, preferably between 7,000 and 30,000. The A block content is preferably about 10 to 50 percent, more preferably about 10 to 30 percent. Other suitable A blocks may be formed from alpha methyl styrene, t-butyl styrene and other ring alkylated styrenes, as well as mixtures thereof. The B block is an elastomeric conjugated diene, having an average molecular weight from about 5,000 to about 500,000, preferably from about 50,000 to about 200,000. The elastomer preferably comprises about 10 to 90 weight percent, more preferably 40 to 80 weight percent, of either block copolymers having B end blocks, such as A-B diblock copolymers, or pure B elastomer, most preferred are A-B block copolymers having B end blocks.

The tackifying components for the elastomer-based adhesives generally comprise solid tackifying resin and/or a liquid tackifier or plasticizer. Preferably, the tackifying resin is selected from the group of resins at least partially compatible with the diene B block portion of the elastomeric polymer or block copolymer. Although not preferred, generally, a relatively minor portion of the tackifying resin can include resins compatible with the A block, when present, generally termed endblock reinforcing resins. Generally, these endblock resins are formed from aromatic species.

Suitable liquid tackifier or plasticizers for use in the fastening tape tab adhesive composition include naphthenic oils, paraffinic oils, aromatic oils, mineral oils or low molecular weight rosin esters, polyterpenes and $C_5$ resins The tackifier portion of the pressure-sensitive adhesive generally comprises from 20 to 300 parts per 100 parts of the elastomeric phase. Preferably, this is predominantly solid tackifier, however, from 0 to 25 weight percent, preferably 0 to 10 weight percent for adhesion to polyethylene surfaces, of the adhesive can be liquid tackifier and/or plasticizer.

Other conventional pressure-sensitive adhesives can be used on the fastening tape tab to adhere to the low-adhesion printed backsheet, such as acrylate-based adhesives or adhesives based on other diene or nondiene elastomers or natural rubber.

135 Peel Adhesion from Partially Secured Release Coated Film

Test Panels consisted of 2 inch×5 inch (5.1 cm×12.7 cm) clean steel panels which have had a strip of 0.75 inch (1.9 cm) double-coated adhesive tape affixed along each 2 inch (5.1 cm) edge. A sheet of the release printed film was laid down loosely over the test panel so that it was flat without any wrinkles. The cross-direction of the low-adhesion release printed film was parallel to the long dimension of the test panel. The film was rolled down firmly onto the double-coated adhesive arid any excess film that extended beyond the edge of the test panel was trimmed away.

The adhesive composition of the pressure-sensitive adhesive tape used for testing was 40 weight percent Kraton™ 1111 (a polystyrene-polyisoprene linear block copolymer available from Shell Chemical Co. having approximately 15 percent diblock and 85 percent triblock, and a styrene content of about 21 percent), 47 weight percent Wingtack™ Plus (a solid $C_5$ tackifying resin available from Goodyear Chemical Co.), 13 weight percent Shellflex™ 371 (a naphthenic oil available from Shell Chemical Co.), and 1 weight percent Irganox™ 1076 (a hindered phenol antioxidant available from Ciba-Geigy). The adhesive was hot-melt coated onto a 4 mil (102 microns) clear cast matte/matte polypropylene film backing (polypropylene homopolymer resin used to cast the film was #5A95, available from Shell Chemical Co.). The adhesive coating thickness was 44 microns. Each strip of test tape measured 1 inch×2.5 inch (2.5 cm×6.5 cm) with a paper leader measuring 1 inch×8 inch (2.5 cm×20.3 cm) adhered to the final 0.25 inch (0.6 cm) of the tape. This tape assembly was laid with its long dimension parallel to the long dimension of the panel so that the tape was about equidistant from each end of the panel and centered between each side. No additional pressure was exerted in laying down the tape. The tape was immediately rolled down with two passes of a 4.5 pound (2 kilogram) rubber roller and then was tested.

An Instron™ tensile tester was used for peel testing the samples. The samples were tested at an angle of 135 degrees throughout the peel at a constant crosshead speed of 12.5 inches (30.5 cm) per minute. The peel adhesion values are all given in (grams/2.54 cm) width.

EXAMPLE 1 AND COMPARATIVE EXAMPLE 1

A roll of 1 mil (25.4 micron) embossed polyethylene diaper backsheet film, which was supplied with one side corona treated ("MICROFLEX™" available from Clopay Corporation) was corona treated on the non-corona treated side of the film to give a surface energy of about 38 dynes/cm (0.0038N/cm). These films are not corona treated on both faces as to do so results in the film blocking making it impossible to unwind the film in roll form.

The Example 1 film was then gravure printed in discrete areas, as shown in FIG. 1, with a 5 percent solids aqueous solution of "HITAC™" RA-11 (a modified polyurethane release material available from Mayzo, Inc., Norcross, Ga.) and oven dried at 120° F. (49° C.). The roll used for printing the release material was Pattern No. 140 (140 Ruling Mill Cell V-Shape Plain Diagonal Line Direct Heavy Application) available from International Engraving Corporation, Cedar Grove, N.J.. The line speed was 40 feet/minute (12 meters/minute). Ideally, only enough release material should be applied to impart consistent release characteristics to the printed areas of the film. The coating weight of the release material can be more accurately controlled with more appropriately designed equipment and processes.

For comparison (comparative example 1), the polyethylene diaper backsheet film samples were printed with the release material as described above except that the film was not corona treated on the non-corona treated side prior to printing the release material on that side of the film.

Five individual test tapes were used for testing 135 degree peel adhesion against a single sample of each of the release printed films prepared above in the release printed area. The results are given in Table I.

TABLE I

| Test Tape | Example 1 (135° peel adhesion) | Comparative Example 1 (135° peel adhesion) |
| --- | --- | --- |
| 1 | 99 | 64 |
| 2 | 109 | 847 |
| 3 | 101 | 787 |
| 4 | 118 | 622 |
| 5 | 112 | 734 |

The data shows that the peel adhesion does not significantly increase after peeling multiple test tapes from a single location of a single Example 1 film. This suggests that there is little or no transfer of the release material to the test tape adhesive. By contrast, the comparative example 1 film sample, that had not been corona treated, showed significant increase in peel adhesion after peeling multiple test tapes and severe stretching of the film was observed. This suggests that the release material was not adequately adhered to the comparative example 1 film, which resulted in transfer of the release material to the test tape adhesive.

The 135 degree peel adhesion was also measured for peeling a single test tape from the release printed area of a single sample of the example and comparative example films, followed by four subsequent reapplications of the same test tape onto the same area of the two films where the test tapes had been initially applied. Results are given in Table II.

TABLE II

|  | Example 1 (135° peel adhesion) | Comparative Example 1 (135° peel adhesion) |
| --- | --- | --- |
| Initial Peel | 99 | 66 |
| 1st Reapplication | 106 | 96 |
| 2nd Reapplication | 108 | 125 |
| 3rd Reapplication | 104 | 146 |
| 4th Reapplication | 120 | 164 |

The data shows that there was no significant increase in peel values (increase was within experimental variation) for the example 1 release printed film. This suggests that there was little or no transfer of the release printing to the test tape adhesive. A more significant increase (2.5 times the initial peel value) was observed for the release printed comparative example 1 film. This indicates that there was greater transfer of the release printing to the test tape adhesive.

The 135 degree peel adhesion of a single test tape from five separate samples of the example and comparative example films was also tested. The results are given in Table III.

TABLE III

| Film Sample | Example 1 (135° peel adhesion) | Comparative Example 1 (135° peel adhesion) |
| --- | --- | --- |
| 1 | 90 | 56 |
| 2 | 82 | 23 |
| 3 | 83 | 14 |
| 4 | 90 | 9 |
| 5 | 80 | 8 |

The data shows little variation in peel adhesion after a single test tape had been peeled from five separate example 1 film samples. This suggests that there was little or no transfer of the release material to the test tape adhesive. By contrast, the peel adhesion decreased sharply for the comparative example 1 test tape that had not been corona treated prior to printing of the release material.

Peel adhesion to the release printing was also tested after aging two sets of four example 1 tape/film laminates for 4 hours and 24 hours, respectively, at 100° F. (38° C.). Heat aging did not result in significant changes in peel adhesion. The test results are given in Table IV.

TABLE IV

|  | 135° Peel Adhesion |
| --- | --- |
| Initial | 68 |
| 4 hrs, 38° C. | 102 |
| 24 hrs, 38° C. | 98 |

EXAMPLE 2

A roll of release printed polyethylene diaper backsheet film was prepared as described in example 1 except that the release material used was an organopolysiloxane-polyurea copolymer. The copolymer used comprised the condensation reaction of an organopolysiloxane diamine with a diisocyanate and a diamine chain extender. The silicone diamine segment had a molecular weight of approximately 5,000 and was prepared as described in U.S. Pat. Nos. 5,214,119 and 5,290,615. The silicone diamine was then reacted with "JEFFAMINE™" DU-700 (available from Texaco Co.), 1,3-diaminopentane, and isophorone diisocyanate to provide a polymer with about 20 weight percent silicone, 25 weight percent "JEFFAMINE™" segment and 55 weight percent hard segment. The organopolysiloxane-polyurea was printed from a 5 percent solids isopropanol solution and oven dried at 140° F. (60° C.). The line speed was 70 feet/minute (21 meters/minute). Five individual test tapes were used for testing for 135 degree peel adhesion against a single sample of the release printed film as described in example 1. The results are given in Table V.

TABLE V

| Test Tape | Example 2 (135° peel) |
| --- | --- |
| 1 | 89 |
| 2 | 90 |
| 3 | 92 |

TABLE V-continued

| Test Tape | Example 2 (135° peel) |
| --- | --- |
| 4 | 94 |
| 5 | 96 |

The data shows that the peel adhesion does not significantly increase after peeling multiple test tapes from the same location of a single film sample.

The 135 degree peel adhesion was also measured for peeling a single test tape from the release printed area of a single sample of the release printed film, followed by four subsequent reapplications of the test tape onto the same area of the film where the tape had been initially applied. Results are given in Table VI.

TABLE VI

|  | Example 2 (135° Peel) |
| --- | --- |
| Initial Peel | 85 |
| 1st Reapplication | 70 |
| 2nd Reapplication | 74 |
| 3rd Reapplication | 81 |
| 4th Reapplication | 71 |

The data shows little variation in peel adhesion after reapplying the test tape several times onto the same area of the example 2 film, where the tape had been initially applied.

The 135 degree peel adhesion was also measured for peeling a single test tape from five separate samples of the example 2 release printed film. The results are given in Table VII.

TABLE VII

| Film Sample | Example 2 (135° Peel) |
| --- | --- |
| 1 | 78 |
| 2 | 79 |
| 3 | 75 |
| 4 | 76 |
| 5 | 79 |

The data shows little variation in peel adhesion after the single test tape had been peeled from a number of the example 2 film samples.

Peel adhesion was also tested after aging two sets of four example 2 tape/film laminates 4 hours and 24 hours, respectively, at 100° F. (38° C.). Heat aging did not result in significant changes in peel adhesion. The test results are given in Table VIII.

TABLE VIII

|  | 135° Peel |
| --- | --- |
| Initial | 78 |
| 4 hrs, 100° F. | 69 |
| 24 hrs, 100° F. | 87 |

EXAMPLES 3–6

A roll of release printed polyethylene film was prepared in a manner similar to that described for Example 1 except that instead of corona treating the non-corona treated film side, that film side was coated with a primer solution and then release printed. The primer solutions used are indicated in Table IV. The primers were gravure coated from 5 weight percent solutions using a Pattern No. 200 roll (Pyramid Cell for Flexographic Printing) available from International Engraving Corporation, Cedar Grove, N.J.. The primer coated film was then oven dried at 49° C. The line speed was (12 m/minute).

The primer coated film was then gravure printed with a 2 percent solids aqueous solution of the "HITAC™" RA-11 release material and was oven dried at 120° F. (49° C.). The line speed was 40 feet/minute (12 m/min). The roll used for printing the release material was the same Pattern No. 200 roll that was used for coating the primer solution.

Another roll of release printed polyethylene diaper backsheet film was prepared as described above except that instead of coating the non-corona treated side of the film with a primer solution, the non-corona treated side of the film was subjected to a flame treatment. A ribbon burner at 4300 BTU/hr/in was used with a premixed natural gas/air flame (air to natural gas ratio was 10.3:1). The distance between the ribbon burner and the film was 7 mm and the film was treated against a chilled nip roll. The line speed was 150 meters/minute. This resulted in a film surface energy of greater than 52 dynes/cm. The 135 degree peel adhesion was measured for peeling a single test tape from a single sample of the release printed film, followed by four subsequent reapplications of one of the test tapes onto the same area of the film where that tape had been initially applied. Results are given in Table IX.

TABLE IX

| Film Treatment | Example 3 CP-347W[1] primer | Example 4 CP-349W[1] primer | Example 5 CP-310W[1] primer | Example 6 Flame Treatment |
| --- | --- | --- | --- | --- |
| Initial Peel | 236 | 254 | 172 | 252 |
| 1st Reapplication | 266 | 270 | 185 | 253 |
| 2nd Reapplication | 301 | 300 | 208 | 257 |
| 3rd Reapplication | 304 | 286 | 225 | 286 |
| 4th Reapplication | 340 | 336 | 214 | 289 |

[1]CP-347W, CP-349W, and CP310W are all available from Eastman Chemical Co., Kingsport, TN. They are adhesion promoter dispersions that are oil-in-water type emulsions based on Eastman CPO.

The data shows a minor increase in peel adhesion after reapplying the same tape to the same location on the same sample of release printed film several times. The films stretched very slightly on peeling and then recovered.

EXAMPLE 7, AND COMPARATIVE EXAMPLE 2

A roll of release printed polyethylene diaper backsheet film was prepared in a manner similar to that described for in Example 1 above except that the film was pattern printed with polar solvent based ink after corona treating and prior to printing of the release material. The ink printing pattern used was a 2 inch×8 inch (5 cm×20 cm) area of printed teddy bears. This ink pattern printed area was similar in size to a typical frontal reinforcement strip found on disposable diapers as shown in FIG. 1. Five spaced apart patterns were printed across the web which measured approximately 64 inches (1.63 meters) in width. The pattern printed film was then printed with a release material in and about the pattern printed area and oven dried. The release material used was a 5 weight percent solution of "HITAC™" RA-11 which was printed using a 180 line laser engraved (45 degree random engraving) ceramic flexographic printing roll having a volume of 3.51 billion cubic microns/cm$^2$ (available from Stork Cellramic). The line speed was 183 m/minute. Film samples were taken from each of the five pattern printed and release printed areas across the web and were tested for 135 degree peel adhesion. The 135 degree peel adhesion was measured for peeling a single test tape from each of the five film samples, followed by four subsequent reapplications of one of the test tapes onto the same area of each film sample where that tape had been initially applied. The 135° peel data is summarized in Table X below.

TABLE X

| Film samples | 1 135° Peel | 2 135° Peel | 3 135° Peel | 4 135° Peel | 5 135° Peel |
| --- | --- | --- | --- | --- | --- |
| Initial Peel | 71 | 95 | 75 | 99 | 78 |
| 1st Reapplication | 69 | 107 | 75 | 110 | 75 |
| 2nd Reapplication | 85 | 112 | 78 | 100 | 87 |
| 3rd Reapplication | 82 | 98 | 87 | 99 | 80 |
| 4th Reapplication | 81 | 107 | 81 | 114 | 85 |

The data show a slight increase in peel adhesion after reapplying the same tape to the same location on the same film sample. There was no transfer of the ink and/or release material to the adhesive and the diaper backsheet film did not tear or stretch on peeling of the tapes.

For comparison (comparative example 2), a roll of film was also prepared that had not been corona treated prior to pattern printing and subsequent printing of the release material. This film was tested as described above. The data is summarized in Table XI.

TABLE XI

| | 1st Pattern | 2nd Pattern | 3rd Pattern | 4th Pattern | 5th Pattern |
| --- | --- | --- | --- | --- | --- |
| Initial Peel | 171 | 200 | 203 | 229 | 204 |
| 1st Reapplication | 205 | 241 | 239 | 249 | 252 |
| 2nd Reapplication | 241 | 289 | 246 | 285 | 278 |
| 3rd Reapplication | 279 | 293 | 283 | 310 | 337 |
| 4th Reapplication | 297 | 335 | 304 | 330 | — |

This data shows a more significant increase in peel adhesion after reapplying the adhesive tape several times to the same location on the comparative example 2 pattern and release printed films. In all cases, there was transfer of the ink to the adhesive tape which is undesirable. The films stretched very slightly on peeling and then recovered.

All example films were formed into rolls after printing with a pattern of the low-adhesion release material. These film rolls could be easily unwound without blocking despite the fact that more than 75 percent of the printed film surface for all the films were not printed with the low adhesion material. Generally at least 10 percent of the film printed face is release printed. At levels lower than this film blocking could occur.

I claim:

1. A roll of nonblocking thermoplastic film consisting essentially of a film having two faces each of said two faces having a surface energy of greater than about 33 dynes/cm$^2$, one of said two faces printed with a low-adhesion material by coating a curable 100 percent solids, polar solvent or aqueous based low-adhesion material over from 10 to 75 percent of said one film face, the remaining portion of said one film face not printed with low-adhesion material, the film thickness being less than about 50 microns wherein the film can be unwound without blocking.

2. The roll of nonblocking thermoplastic film of claim 1 wherein the film is a thermoplastic polyolefin or polyolefin blend film or coextruded film.

3. The roll of nonblocking thermoplastic film of claim 2 wherein the polyolefin film is a polyethylene or polyethylene blend film or coextruded film.

4. The roll of nonblocking thermoplastic film of claim 1 wherein said one film face printed with low-adhesion material has a surface energy of greater than about 40 dynes/cm.

5. The roll of nonblocking thermoplastic film of claim 1 wherein the printed low-adhesion material is a continuous printed pattern.

6. The roll of nonblocking thermoplastic film of claim 4 wherein said one film face is corona treated.

7. The roll of nonblocking thermoplastic film of claim 4 wherein both of said two film faces are corona treated.

8. The roll of nonblocking thermoplastic film of claim 1 wherein the printed low-adhesion material is in the form of one or more strips.

9. The roll of nonblocking thermoplastic film of claim 1 wherein the film has a thickness of less than about 35 microns.

* * * * *